United States Patent
Zhao

(10) Patent No.: US 10,288,866 B2
(45) Date of Patent: May 14, 2019

(54) OPTICAL SYSTEM OF A STEREO VIDEO ENDOSCOPE, STEREO VIDEO ENDOSCOPE AND METHOD FOR OPERATING AN OPTICAL SYSTEM OF A STEREO VIDEO ENDOSCOPE

(71) Applicant: OLYMPUS WINTER & IBE GMBH, Hamburg (DE)

(72) Inventor: Jianxin Zhao, Hamburg (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 9 days.

(21) Appl. No.: 15/640,794

(22) Filed: Jul. 3, 2017

(65) Prior Publication Data
US 2018/0011308 A1 Jan. 11, 2018

(30) Foreign Application Priority Data
Jul. 8, 2016 (DE) .................. 10 2016 212 470

(51) Int. Cl.
*A61B 1/00* (2006.01)
*A61B 1/04* (2006.01)
*G02B 23/24* (2006.01)

(52) U.S. Cl.
CPC ...... *G02B 23/2415* (2013.01); *A61B 1/00006* (2013.01); *A61B 1/00096* (2013.01);
(Continued)

(58) Field of Classification Search
CPC ............ G02B 23/2415; A61B 1/00193; A61B 1/00002; H04N 13/189; H04N 13/204
See application file for complete search history.

(56) References Cited

U.S. PATENT DOCUMENTS 5,522,789 A * 6/1996 Takahashi .......... A61B 1/00188
600/166
5,557,454 A * 9/1996 Takahashi .......... A61B 1/00193
348/45
(Continued)

FOREIGN PATENT DOCUMENTS

DE 102013215422 A1 2/2015
DE 102013217449 A1 3/2015
(Continued)

OTHER PUBLICATIONS

Nakamura, English Translation of WO-2010079817, 2010.*
Japanese Office Action dated Nov. 20, 2018 in Japanese Patent Application No. 2017-133926.

*Primary Examiner* — Fernando Alcon
(74) *Attorney, Agent, or Firm* — Scully, Scott, Murphy & Presser, P.C.

(57) ABSTRACT

An optical system for a stereo video endoscope, a stereo video endoscope and a method for operating an optical system. The optical system includes a distal optical assembly and a proximal optical assembly with a left lens system channel and a right lens system channel. The distal optical assembly couples light incident from an object space into the left lens system channel and into the right lens system channel of the proximal optical assembly. The distal optical assembly is an optical assembly with an adjustable focal length, wherein a change in the focal length causes a displacement of an axis intersection point in the object space.

6 Claims, 4 Drawing Sheets

Figure 1:
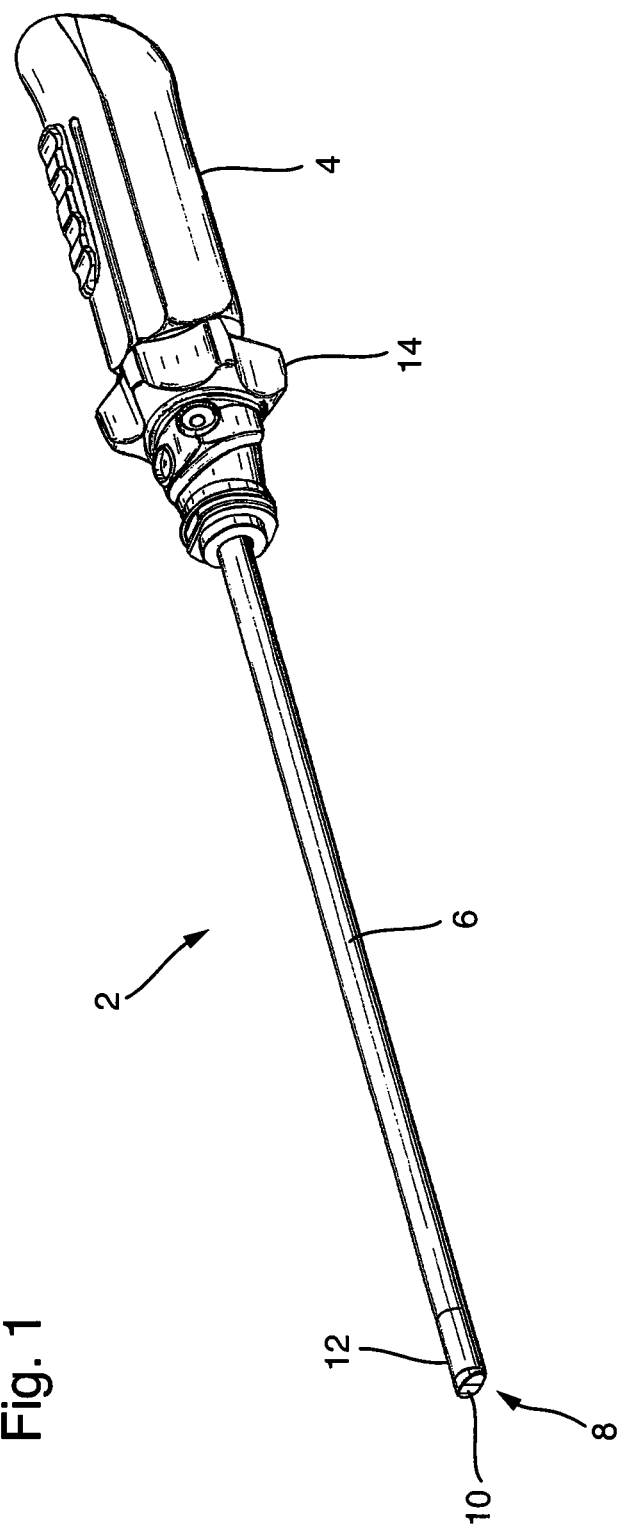

(52) U.S. Cl.
CPC ...... *A61B 1/00188* (2013.01); *A61B 1/00193* (2013.01); *A61B 1/04* (2013.01); *G02B 23/2438* (2013.01); *G02B 23/2453* (2013.01)

(56) References Cited

U.S. PATENT DOCUMENTS

| | | | | |
|---|---|---|---|---|
| 5,971,915 | A | * | 10/1999 | Yamamoto ......... A61B 1/00193 600/111 |
| 6,219,182 | B1 | | 4/2001 | McKinley |
| 2007/0058249 | A1 | | 3/2007 | Hirose et al. |
| 2009/0096865 | A1 | | 4/2009 | McKinley |
| 2010/0208046 | A1 | * | 8/2010 | Takahashi ......... A61B 1/00193 348/65 |
| 2012/0075448 | A1 | * | 3/2012 | Namii ................ A61B 1/00193 348/68 |
| 2013/0038689 | A1 | * | 2/2013 | McDowall ......... G02B 27/0075 348/45 |
| 2016/0154231 | A1 | | 6/2016 | Zhao et al. |

FOREIGN PATENT DOCUMENTS

| | | | | |
|---|---|---|---|---|
| JP | 2013-515973 | A | | 5/2013 |
| JP | 2013-218238 | A | | 10/2013 |
| JP | 2014-110910 | A | | 6/2014 |
| WO | 2010/079817 | A1 | | 7/2010 |
| WO | WO-2010079817 | A1 | * | 7/2010 ......... A61B 1/00188 |

* cited by examiner ial viewing axis, in the examination or operative field.

OPTICAL SYSTEM OF A STEREO VIDEO ENDOSCOPE, STEREO VIDEO ENDOSCOPE AND METHOD FOR OPERATING AN OPTICAL SYSTEM OF A STEREO VIDEO ENDOSCOPE

CROSS-REFERENCE TO RELATED APPLICATION

The present application claims benefit to DE 10 2016 212 470.6 filed on Jul. 8, 2016, the entire contents of which is incorporated herein by reference.

BACKGROUND

Field

The present application relates to an optical system of a stereo video endoscope, comprising a distal optical assembly and a proximal optical assembly, wherein the proximal optical assembly comprises a left lens system channel with a left optical axis and a right lens system channel with a right optical axis, and wherein the left and the right lens system channel are similarly designed and the left and the right optical axis are aligned parallel to each other, and wherein the distal optical assembly is configured to couple light incident from an object space into the left lens system channel and into the right lens system channel of the proximal optical assembly, and wherein the distal optical assembly defines an axis intersection point in the object space, in which a left viewing axis of the left lens system channel and a right viewing axis of the right lens system channel intersect.

Furthermore, the present application relates to stereo video endoscope with such an optical system as well as a method for operating an optical system of a stereo video endoscope, wherein the optical system comprises a distal optical assembly and a proximal optical assembly and wherein the proximal optical assembly comprises a left lens system channel with a left optical axis and a right lens system channel with a right optical axis, and wherein the left and the right lens system channel are similarly designed and the left and the right optical axis are aligned parallel to each other, and wherein the distal optical assembly couples light incident from an object space into the left lens system channel and into the right lens system channel of the proximal optical assembly, and wherein the distal optical assembly defines an axis intersection point in the object space, in which a left viewing axis of the left lens system channel and a right viewing axis of the right lens system channel intersect.

Prior Art

Video endoscopes, in which the light entering at a distal tip of an endoscope shaft is directed through an optical system onto one or more images sensors, are known in different designs. There are endoscopes with a direct view, a so-called 0° viewing direction, endoscopes with a lateral viewing direction as well as endoscopes with an adjustable viewing direction (also called V-DOV endoscopes).

Moreover, stereo video endoscopes are known, which are designed to record a stereoscopic image pair or respectively two stereoscopic video channels. With such instruments, it is possible to create a 3D image of an examination or operating room lying distally in front of the end of the endoscope shaft. In the case of stereo video endoscopes, the two optical channels are recorded from a slightly different viewing direction. The left channel faces in the direction of a left viewing axis, which joins an angle with a right viewing axis, in which direction the right channel faces. The left and the right viewing axes meet at an axis intersection point in the object space. This point corresponds in humans with the point of intersection at which the viewing lines of both human eyes meet.

The two channels of the stereo video endoscope are spaced from each other by a stereo base, are offset or displaced with respect to each other. The right and the left image channels are recorded simultaneously and are made available to a user via especially suitable playback devices, for example on a 3D screen or via 3D video glasses. This shows a 3D image of the objects present in the examination or operative field.

An optical system of a stereo video endoscope with a lateral viewing direction is known from DE 10 2013 215 422 A1. The system comprises a sideways-facing distal optical assembly. It is arranged behind an entrance window, which shuts off the endoscope shaft from an exterior. The distal optical assembly comprises—observed in the light incidence direction—in succession an entrance lens, an optical deflection unit and an exit lens. A left and a right lens system channel of a proximal optical assembly follow further on the exit lens of the distal optical assembly as observed in the light incidence direction. The two lens system channels each have their own optical axis and are configured to image the left and the right channel on a left and a right image sensor. The optical system comprises a single common distal optical assembly and two discrete proximal optical assemblies, namely the left and the right lens system channel.

A further optical system of a stereo video endoscope is known from DE 10 2013 217 449 A1. This system allows a variable viewing direction. A prism unit serves to change the viewing direction, which can be pivoted both about a vertical as well as a horizontal axis. The two rotational axes are perpendicular on a longitudinal axis of the endoscope shaft. The prism unit comprises a central deflection unit and two pairs of deflection prisms, which are respectively arranged on opposite-lying sides of the central deflection unit. Like the optical system known from DE 10 2013 215 422 A1, a single and common distal optical assembly is in turn configured to couple light incident from an object space into the optical system into the left lens system channel and into the right lens system channel.

Modern stereo video endoscopes offer high image resolutions. Their image sensors have a large number of pixels and accordingly a very small pixel size. The optical systems of such instruments have optical systems (lenses) with a large aperture, i.e. a small f-number. However, these optical systems only offer a small sharpness depth. It is thus required to focus the imaging optical systems of the left and the right lens system channel on a best working point so that an object located in the object space is imaged on the image sensors of the left and right lens system channel. This best working point is also denominated as best operating point.

SUMMARY

An object is to specify an optical system of a stereo video endoscope, a stereo video endoscope and a method for operating an optical system of a stereo video endoscope, wherein an improved 3D representation should be possible.

Such object can be solved by an optical system of a stereo video endoscope, comprising a distal optical assembly and a proximal optical assembly, wherein the proximal optical assembly comprises a left lens system channel with a left optical axis and a right lens system channel with a right optical axis, and wherein the left and the right lens system channel are similarly configured and the left and the right optical axis are aligned parallel to each other, and wherein the distal optical assembly is configured to couple light incident from an object space into the left lens system channel and into the right lens system channel of the proximal optical assembly, and wherein the distal optical assembly defines an axis intersection point in the object space, in which a left viewing axis of the left lens system channel and a right viewing axis of the right lens system channel intersect, wherein the distal optical assembly is an optical assembly with an adjustable focal length, wherein a change in the focal length of the distal optical assembly causes a displacement of the axis intersection point in the object space in a direction along an optical axis of the distal optical assembly.

The change in the focal length of the distal optical assembly takes place similarly to the zoom action of a zoom lens, as known from photography. Such lenses are also called a vario objective lens, vario system, vario focus or transfocator. The displacement of the axis intersection point in the object space can take place parallel to the optical axis of the distal optical assembly. Furthermore, the distal optical assembly in the operation of the optical system can couple light incident from the object space into the left lens system channel and into the right lens system channel of the proximal optical assembly.

The focusing of the left lens system channel and of the right lens system channel permits a sharp imaging of objects located in the object space. However, in this process, the zero level of the 3D image remains unchanged although the respectively sharply imaged objects are located at different distances from the distal tip of the endoscope. In other words, the axis intersection point, at which the viewing axes of the left lens system channel and of the right lens system channel cross, can lie both in front of as well as behind the plane, in which the objects are imaged sharply on the image sensors of the lens system channels.

In the 3D representation of the image created of such an object, this effect leads to the 3D image appearing to lie both in front of as well as behind the surface of the screen. However, the zero level of the 3D representation ideally lies in the plane of the screen surface. The displacement of the 3D representation in the depth direction is often considered by the user as uncomfortable and strenuous for the eyes.

Accordingly, with the help of the optical system it is possible to achieve a displacement of the 3D zero level of the 3D representation via a displacement of the axis intersection point through a change in the focal length of the distal optical assembly. The zero level can be placed at any position. The user decides on his/her own and sets up the system so that the 3D representation feels comfortable. It is possible to place the 3D zero level in a plane in which the surface of the monitor extends.

The 3D representation possible with the optical system is more comfortable. Work with such a system is less tiring. This aspect is very significant and highly relevant for a stereo video endoscope. An endoscope ultimately serves as a technical aid for a surgeon. The surgeon generally experiences a high level of stress during his/her work. The 3D representation provided by a surgical instrument should not raise the surgeon's stress level further. Surgical interventions often last for extended periods of time. It is thus important that the surgeon is able to observe the 3D representation without getting tired.

For the imaging of objects present in an object space, the optical system of the stereo video endoscope can comprise a left image sensor and a right image sensor. The image created by the left lens system channel is imaged on the left image sensor. The right lens system channel images on the right image sensor. The image sensors can concern sensors with a high resolution, for example HD, 4K and subsequent technologies.

According to an embodiment, it is provided that the distal optical assembly comprises at least one displaceable optical element. The displacement of this optical element causes a change in the focal length of the distal optical assembly. It is also possible that the distal optical assembly comprises more than one displaceable optical element. Such a group of elements then effectuates for example the change in the focal length. Besides the change in the focal length, the displacement of the element or of the optical elements effectuates for example an elongation or displacement of the main plane of the distal optical assembly.

According to a further embodiment, it is provided that the distal optical assembly in a light incidence direction comprises in succession an entrance lens, a deflection prism and an exit lens. The exit lens can be the displaceable optical element.

In other words, for adjusting the 3D zero level, respectively a common lens, which can be the exit lens of the distal optical assembly, as well as respectively for example a lens in the individual lens system channels are displaced in order to focus the image. Both the sharpness of the image as well as the position of the zero level of the 3D representation are thereby checked.

According to a further embodiment, the distal optical assembly can comprise a zoom drive. The optical system can further comprise a control unit coupled with the zoom drive, wherein the control unit is configured to control the zoom drive. The control unit can be configured to control the zoom drive such that the axis intersection point can be set alternatively to a best operating point in the near range or to a best operating point in the far range. This means that the control unit in the operation of the optical system controls the zoom drive such that the axis intersection point can be set alternatively to a best operating point in the near range or to the best operating point in the far range. The best operating point in the near range and the best operating point in the far range lie in the object space. The best operating point in the far range is further removed from the distal optical assembly than the best operating point in the near range.

The zoom drive can be coupled with the displaceable optical element. It is also provided that the zoom drive can be coupled with several optical elements. The drive is configured for displacing/shifting and for positioning the displaceable optical element or the displaceable optical elements. The displacement causes the axis intersection point to be set alternatively to the best operating point in the near range or the best operating point in the far range.

Furthermore, the best operating point in the near range and the best operating point in the far range maintain a minimum distance from each other. This minimum distance is for example a few millimeters or even a few centimeters. The best operating point in the near range lies further away in particular in a near range. The best operating point in the far range also lies in particular in a far range. For example, it is provided that the best operating point in the near range lies on a front boundary of the near range. For example, it is also provided that the best operating point in the far range lies on a front boundary of the far range. A front boundary of the near or far range lies the closest to the distal optical assembly. Furthermore, the near range and the far range partially overlap. Both the near range as well as the far range lie in the object space. The near range is thereby closer to the entrance lens of the distal optical system than the far range.

More than two points as well as more than two areas can be provided. Accordingly, the control unit can be configured to set the axis intersection point to several best operating points. The control unit can be configured to adjust infinitely the axis intersection point. The axis intersection point is thus variably displaceable along a direction, which lies at least approximately parallel to the optical axis of the distal lens group.

The left lens system channel can comprise at least one displaceable left optical element and the right lens system channel at least one displaceable right optical element. By displacing the left optical element, the sharpness of an image of an object located in the object space changes in the left lens system channel. By displacing the right optical element, the sharpness of an image of the object located in the object space changes in the right lens system channel. The control unit can be configured to determine to query or to measure, a left or a right object distance value and to control the zoom drive such that the axis intersection point is changed as a function of the left or right object distance value.

The object distance value is a parameter that can be derived from the position of the moveable left or right optical element in the respective lens system, which indicates a distance, in which the object sharply imaged by the respective channel is located. In the case of a photographic objective lens, an object distance value would be the distance specified on a sharpness adjustment ring.

The zoom drive can be controlled such that it displaces the axis intersection point proportionally to such an object distance value. For example, the axis intersection point will always lie in a plane, in which objects from the left lens system channel or from the right lens system channel are sharply imaged. For this, the control unit can be controlled depending on the object distance value of the left or the right lens system channel. In other words, the position of the axis intersection point of the sharpness plane of one of the two lens system channels is thus tracked. A coupling of the zoom action of the distal optical assembly to the focusing of the lens system channel(s) thus takes place. This coupling can take place mechanically. A common drive for the focusing and for the adjustment of the axis intersection point can be used by changing the focal length of the distal optical assembly. It is also provided that there is an electronic coupling via the control unit.

The axis intersection point can be displaced in intervals when the object distance value changes. For example, it can be queried whether the object distance value lies in a near range or in a far range. If the object distance value lies in the near range, the control unit can be controlled such that the axis intersection point is adjusted to the best operating point in the near range. If it is determined that the plane, in which the object is sharply imaged, lies in the far range, then the axis intersection point can be set through corresponding activation of the zoom drive to the best operating point in the far range.

Such object can be further solved by a stereo video endoscope comprising an optical system according to one or more of the previously named embodiments.

The same or similar advantages apply to the stereo video endoscope as were previously mentioned with respect to the optical system. The stereo video endoscope can provide a 3D representation, which can be considered non-tiring. This aspect is particularly relevant for a surgical instrument like the stereo video endoscope shows. Stereo video endoscopes are often used in long-lasting operations. It is very important for the surgeon that he/she has a working tool which allows him/her to work for a longer period of time without getting tired.

Furthermore, such object can be solved by a method for operating an optical system of a stereo video endoscope, wherein the optical system comprises a distal optical assembly and a proximal optical assembly, and wherein the proximal optical assembly comprises a left lens system channel with a left optical axis and a right lens system channel with a right optical axis, and wherein the left and the right lens system channel are similarly designed and the left and the right optical axis are aligned parallel to each other, and wherein the distal optical assembly couples light incident from an object space into the left lens system channel and into the right lens system channel of the proximal optical assembly, and wherein the distal optical assembly defines an axis point of intersection in the object space, in which a left viewing axis of the left lens system channel and a right viewing axis of the right lens system channel intersect, wherein for the imaging of objects in the object space, which are located at different distances from the distal optical assembly, a focal length of the distal optical assembly is changed, wherein a change in the focal length of the distal optical assembly causes a shift in the axis intersection point in the object space in a direction along an optical axis of the distal optical assembly.

The same or similar advantages apply to the method for operating the optical system as were previously mentioned with respect to the optical system.

The at least one optical element of the distal optical assembly can be displaced in order to change the focal length of the distal optical assembly.

Furthermore, the distal optical assembly can comprise a zoom drive, wherein the axis intersection point is displaced with the zoom drive. With the zoom drive, the axis intersection point can be set alternatively to a best operating point in the near range or to a best operating point in the far range. The best working position in the near range as well as the best operating point in the far range thereby lie in the object space, wherein the best operating point in the far range is further removed from the distal optical assembly than the best operating point in the near range.

The left lens system channel can comprises at least one displaceable left optical element and the right lens system channel at least one displaceable right optical element, wherein by displacing the left optical element the sharpness of an image of an object located in an object space in the left lens system channel is changed and by displacing the right optical element the sharpness of an image of the object located in the object space in the right lens system channel is changed, and wherein a left or a right object distance value is determined and the zoom drive is controlled such that the axis intersection point changes as a function of the left or right object distance value.

Furthermore, the axis intersection point can be changed proportionally to the left or the right object distance value. The axis intersection point can be variably adjusted by the corresponding activation of the zoom drive. For this, it is for example queried whether the left or the right object distance value is located in a certain specified interval. The object distance value is then set for example to the middle of the interval. Thus, if the object distance value is located for example in a near range, then the zoom drive is activated such that the axis intersection point lies on the best operating point in the near range. The same applies for example if it is determined that the object distance value lies in a far range. The axis intersection point is then set to the best operating point in the far range.

Further features will become apparent from the description of embodiments together with the claims and the included drawings. Embodiments can fulfill individual characteristics or a combination of several characteristics.

Figure 2:
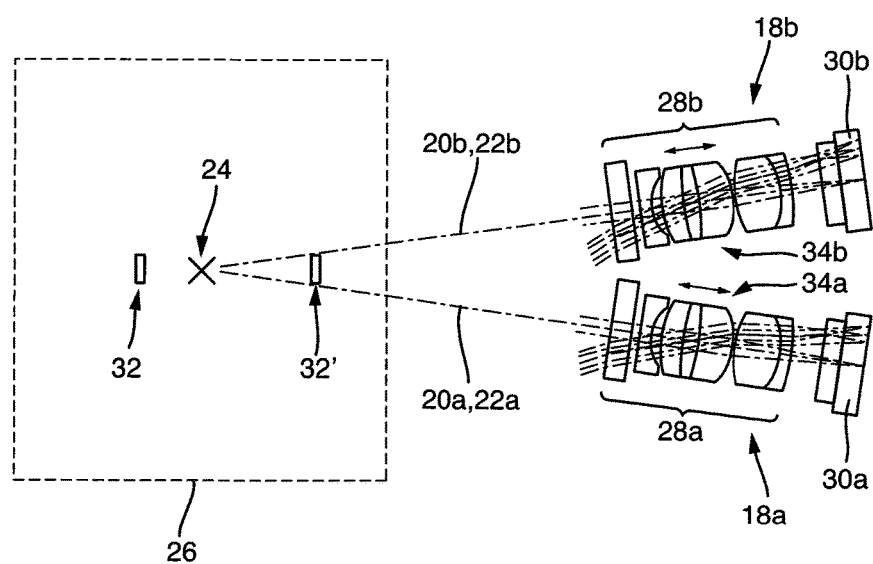
Figure 3:
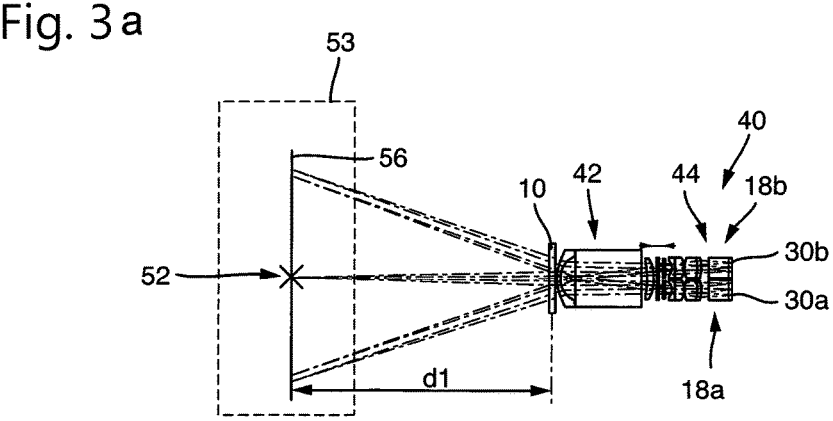
Figure 3:
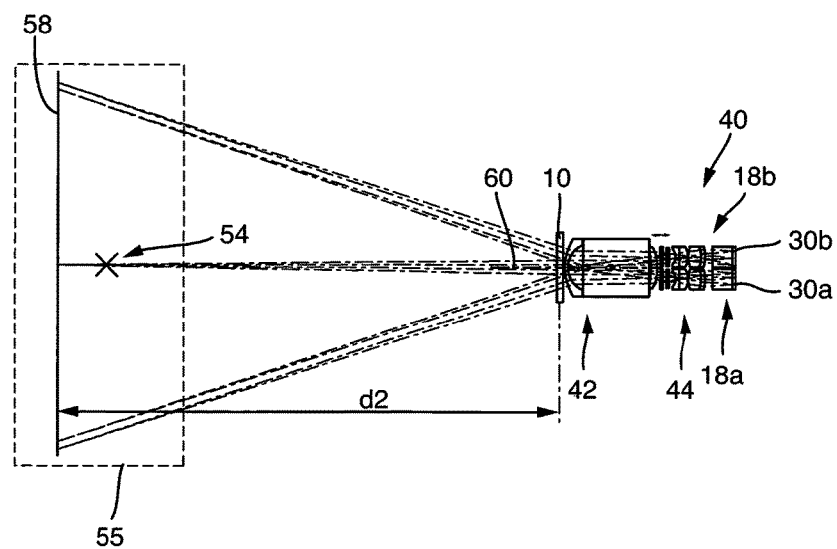
Figure 4A:
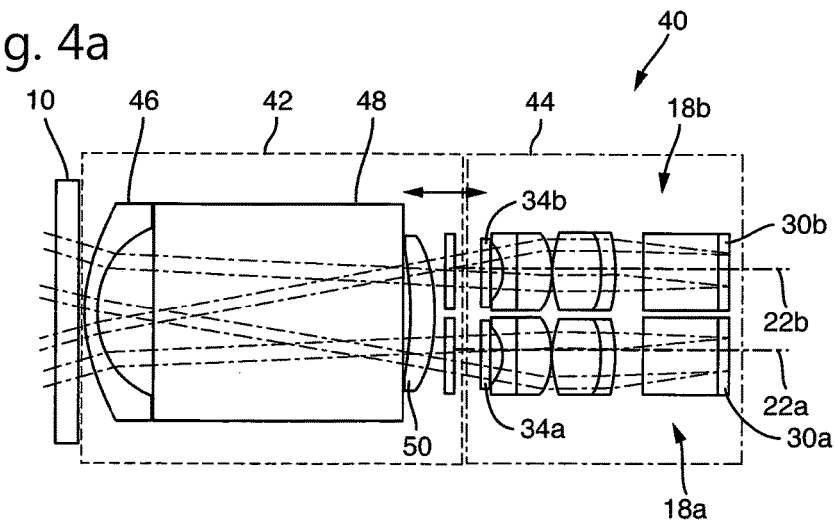
Figure 4B:
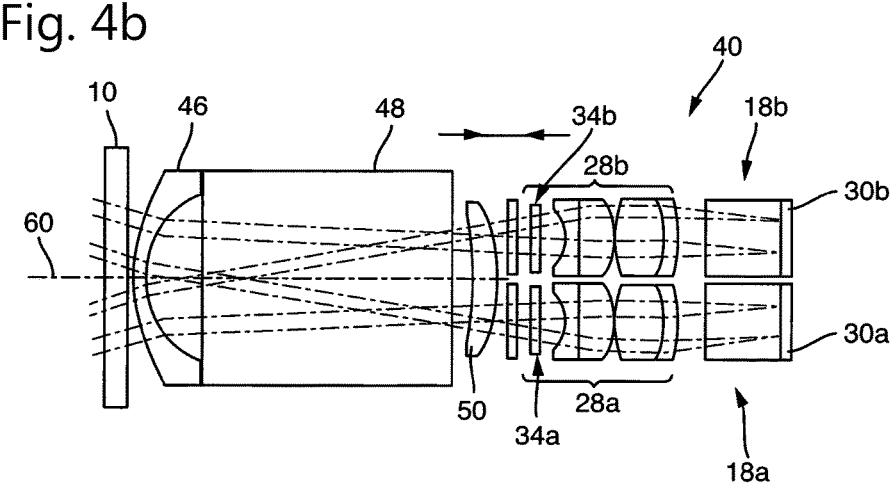

The invention is described below, without restricting the general idea of the invention, based on exemplary embodiments in reference to the drawings, wherein the drawings are expressly referred to with regard to the disclosure of all details that are not explained in greater detail in the text. The figures show the following:

FIG. 1 illustrates a schematically simplified representation of a stereo video endoscope comprising an optical system, FIG. 2 illustrates a schematically simplified sketch of the stereoscope capturing of objects with a left and a right lens system channel without providing a 3D zero level displacement, FIGS. 3a and 3b respectively illustrate a schematic and simplified representation of an optical system of a stereo video endoscope wherein the optical system is set to a near range (FIG. 3a) or to a far range (FIG. 3b) and FIGS. 4a and 4b further schematically illustrate simplified views of an optical system, which is set to a near range (FIG. 4a) or to a far range (FIG. 4b).

In the drawings, the same or similar types of elements and/or parts are provided with the same reference numbers so that a re-introduction is omitted.

DETAILED DESCRIPTION

FIG. 1 shows in a schematically simplified representation of a stereo video endoscope 2 in a perspective representation. The stereo video endoscope 2 comprises a proximal handle 4, to which for example a rigid endoscope shaft 6 connects. An entrance window 10, through which light from an operative or observation field enters an optical system (not shown in FIG. 1) of the stereo video endoscope 2, is located on a distal tip 8 of the endoscope shaft 6. The optical system of the stereo video endoscope 2 is arranged for example in a distal section 12 of the endoscope shaft 6. The optical system images onto image sensors. The image sensors have for example a high resolution such as for example HD, 4K or subsequent technologies.

The shown stereo video endoscope 2 can be configured as an instrument with a direct view (0° viewing direction), with a lateral viewing direction or with an adjustable viewing direction. Should a variable or lateral viewing angle be permitted, then the entrance window 10 is designed in a bent and asymmetrical manner. A change in the viewing direction about the longitudinal axis of the endoscope shaft 6 is in turn effectuated by a rotation of the handle 4 about the longitudinal axis of the endoscope shaft 6. The optical system provided in the distal section 12 rotates along during this rotation of the handle 4. To retain the horizontal position of the displayed image, the rotary wheel 14 is held while rotating the handle 4. This causes one or more image sensors within the interior of the endoscope shaft 6 to not follow the rotational movement.

The optical system of the stereo video endoscope 2 comprises a distal optical assembly and a proximal optical assembly. The proximal optical assembly comprises a left lens system channel with a left optical axis and a right lens system channel with a right optical axis. The left and the right lens system channels are structured the same and the left and the right optical axes are aligned parallel to each other. The distal optical assembly is configured to couple light incident from the object space both into the left lens system channel as well as into the right lens system channel of the proximal optical assembly.

If the stereo video endoscope 2 is an instrument with a lateral viewing direction, then its optical system, such as the distal optical assembly of the optical system, is for example structured similarly or the same as disclosed in DE 10 2013 215 422 A1. If the stereo video endoscope 2 is an instrument with a variable viewing direction, then its optical system, such as the distal optical assembly, is for example structured as disclosed in DE 10 2013 217 449 A1. The disclosures both of DE 10 2013 215 422 A1 as well as of DE 10 2013 217 449 A1 are incorporated herein by reference.

The stereo video endoscope is configured to record a stereoscopic image pair or respectively two stereoscopic video channels. It is thus possible to create a 3D image of an object lying in an examination or operation room, which is located distally in front of the distal tip 8. A user of the stereo video endoscope 2 can observe a 3D image of this object with a suitable playback device (not shown), for example a 3D monitor or 3D video glasses.

FIG. 2 shows a schematically simplified illustration, which illustrates a stereoscopic capturing of objects with the help of a left and a right lens system channel of an optical system. The illustration in FIG. 2 represents an arrangement of the zoomed right and left lens system channels in the optical system of the stereo video endoscope 2. The zero level of the optical system is not adjustable. The left and the right lens system channels are arranged at an angle to each other. This is not the case for the optical system of the stereo video endoscope 2; the two lens system channels are arranged parallel (with respect to their optical axes) to each other.

In the illustration shown in FIG. 2, the left lens system channel 18a faces in the direction of a left viewing axis 20a, which coincides with the left optical axis 22a of the left lens system channel 18a. The right lens system channel 18b faces in the direction of a right viewing axis 20b, which coincides with the right optical axis 22b. The left viewing axis 20a and the right viewing axis 20b intersect at an axis intersection point 24 in an object space 26.

In the case of the optical system of the stereo video endoscope 2, the optical axes 22a, 22b of the lens system channels 18a, 18b are aligned parallel with respect to each other. The mechanical structure ensures that the left viewing axis 20a of the left lens system channel 18a and the right viewing axis 20b of the right lens system channel 18b intersect at the axis intersection point 24 in the object space 26. In the case of the optical system of the stereo video endoscope 2, the optical axes 22a, 22b and the viewing axes 20a, 20b do not coincide like in FIG. 2.

A left optical system 28a and a right optical system 28b, which image on a left image sensor 30a or on a right image sensor 30b and respectively form together with it the left or right lens system channel 18a, 18b, are fast optical systems with a large aperture or respectively a low f-number. Such optical systems 28a, 28b have a low depth sharpness so that they must be focused in order to image an object 32, 32' located at different distances away, which is located in the object space 26, onto the image sensors 30a and 30b respectively as sharply as needed. For this, the left optical system 28a comprises a left displaceable lens group 34a, and the right optical system 28b comprises correspondingly an identical right displaceable lens group 34b.

By displacing the displaceable lens group 34a and 34b, it is possible to display the plane, in which objects are sharply imaged on the sensor 30a, 30b, along the optical axis 22a, 22b. It is thus possible through the focusing of the left or respectively right optical system 28a, 28b to image respectively the object 32 as well as the object 32' sharply on the image sensor 30a and 30b. During the focusing, the axis intersection point 24, in which the left and right viewing axes 20a, 20b intersect, remains unchanged. In other words, an object 32 lying behind the axis intersection point 24 or an object 32' lying in front of the axis intersection point 24 is thus sharply imaged. The terms "behind" and "in front" refer to the separation distance of the objects 32, 32', starting from the left and from the right lens system channel 18a, 18b, with respect to the separation distance of the axis intersection point 24.

The imaging of objects, which lie in front of or behind the axis intersection point 24, leads to a displacement of the 3D zero level in the 3D representation. The respectively imaged object 32, 32' appears to lie in front of or behind a surface of a screen, which provides the 3D view of the object 32, 32'. In many cases, such a 3D representation is found to be uncomfortable and tiring.

In order to counteract this effect, the optical system of the stereo video endoscope 2 comprises a distal optical assembly with an adjustable focal length. Through the change in the focal length, it is possible to displace the axis intersection point 24 in the object space 26 in the direction of an optical axis of the distal optical assembly.

FIGS. 3a and 3b respectively show a schematic and simplified representation of the optical system 40, wherein the optical system 40 in the representation in FIG. 3a is set to a near range and in the representation in FIG. 3b to a far range. FIGS. 4a and 4b show further schematically simplified views of the optical system 40, which is set to the near range (FIG. 4a) or to the far range (FIG. 4b). The optical system 40 is described with reference to FIGS. 3a, 3b, 4a and 4b.

The optical system 40 comprises a distal optical assembly 42 (surrounded in FIG. 4a with a dashed line) as well as a proximal optical assembly (surrounded in FIG. 4a with a dotted line). As already mentioned, the proximal optical assembly 44 comprises the left lens system channel 18a and the right lens system channel 18b. The two lens system channels 18a, 18b are arranged such that the left optical axis 22a of the left lens system channel 18a and the right optical channel 22b of the right lens system channel 18b are aligned parallel to each other (see FIG. 4a). The left and the right lens system channels 18a, 18b are also structured in the same or similar manners. They respectively comprise an optical system 28a, 28b (see FIG. 4b), with which light is imaged onto a left or a right image sensor 30a, 30b. For focusing, the left and the right optical system 28a, 28b respectively comprise a displaceable lens group 34a, 34b or respectively a displaceable lens. The focusing process is clear when comparing the images in FIGS. 4a and 4b. The lens group 34a, 34b is respectively located at a different position.

The distal optical assembly 42 is configured to couple light incident from the object space 26 both into the left as well as into the right lens system channel 18a, 18b. The distal optical assembly 42 is an optical assembly with an adjustable focal length. This is caused by the displacement of a displaceable optical element, which includes the distal optical assembly 42. In the exemplary embodiments shown, the distal optical assembly 42 in the light incidence direction comprises in succession an entrance lens 46, a deflection prism 48 as well as an exit lens 50. Furthermore, FIGS. 4a and 4b show the entrance window 10, which closes off the interior of the endoscope shaft 6 from an exterior (FIG. 1). The change in the focal length of the distal optical assembly 42 takes place through the displacement of the exit lens 50. This emanates for example from a comparison of FIGS. 4a and 4b. The exit lens 50 is thus for example the displaceable optical element. A change in the focal length of the distal optical assembly 42 causes a displacement of the axis intersection point 24 in the object space 26. This displacement takes place in a direction along an optical axis 60 of the distal optical assembly 42 (see FIGS. 3b and 4b).

The distal optical assembly 42 is provided for example with a zoom drive (not shown) or comprises it. Furthermore, a control unit coupled with this zoom drive (also not shown) is provided in the optical system 40. The control unit is configured to drive infinitely the zoom drive but also to adjust certain positions or settings. It is provided in particular that the control unit drives the zoom drive such that the axis intersection point 24 lies on a best operating point in the near range 52 (see FIG. 3a) or on a best operating point in the far range 54 (see FIG. 3b).

The best operating point in the near range 52 and the best operating point in the far range 54 lie in the object space 26. As shown by a comparison of FIGS. 3a and 3b, the best operating point lies in the far range 54 further removed from the distal optical assembly 42 than the best operating point in the near range 52. For example, in this connection, a separation distance between the entrance window 10 and the respective position of the near or respectively best operating point in the far range 42, 54 is referenced. The best operating point in the near range 52 lies in a near range 53. The best operating point in the far range 54 lies in a far range 55. The distal optical assembly 42 is configured for example such that its displaceable optical element, i.e. for example the exit lens 50, can be positioned in two different positions so that the axis intersection point 24 lies alternatively on the best operating point in the near range 52 or on the best operating point in the far range 54.

For the imaging of objects, which lie in the near range 53, the object plane, in which objects can be sharply imaged, and the axis intersection point, which lies on the best working position in the near range 52, lie close enough together so that no appreciable deviations of the 3D zero level can be perceived by the user. If objects that lie in the far range 55 are imaged, the axis intersection point 24 is set to the best working position in the far range 54. Objects in the far range 55 can again be sharply imaged without the user perceiving an appreciable deviation in the 3D zero level for example of a surface of the screen. For example, the best operating point in the near range 52 lies in the middle of the near range and the best operating point in the far range 54 lies in the middle of the far range 55.

In contrast to the representation in FIG. 3, the near range 53 and the far range 55 can be configured such that they are directly adjacent to each other. No space would then be provided between the near range 53 and the far range 55.

The adjustment of the distal optical assembly 42 to the near range 53 or the far range 55 takes place for example in that an object distance value is queried from the right or the left lens system channel 18a, 18b. The object distance value is the separation distance in which objects are located that are sharply imaged on the respective sensor 30a, 30b. In the representations in FIG. 3a, these are objects in the near object plane 56, i.e. with object distance value d1. In FIG. 3b, these are objects that lie in the far object plane 58. They have the object distance value d2. The object distance value d1, d2 is measured for example between the plane 56, 58 and the entrance window 10.

If for example the control unit of the optical system 40 determines that the object distance value d1, d2 lies in the near range 53, then it is permitted that the distal optical assembly 42 sets the axis intersection point 24 to the best operating point in the near range 52. In FIG. 3b, the far object plane 58 is distanced from the entrance window 10 by the second object distance value d2. If the control unit of the optical system 40 determines that the second object distance value d2 lies within the far range 55, then the distal optical assembly 42 is set so that the axis intersection point 24 lies on the best operating point in the far range 54.

In other words, the zoom drive of the distal optical assembly 42 is thus configured to change the axis intersection point 24 as a function of the object distance value d1, d2.

For example, in addition to this incremental change, it is also provided that the axis intersection point 24 is continuously updated for the position of the sharply imaged object plane 56, 58. In this case, the focal length of the distal optical assembly 42 would thus be changed for example proportionally to the value of the object distance value. The object distance value d1, d2, based on which the axis intersection point 24 is updated, is determined for example based on an object distance value delivered by the left or by the right lens system channel 18a, 18b.

In the case of a method for operating the optical system 40 of a stereo video endoscope 2, a focal length of the distal optical assembly 42 is changed for the imaging of objects 32, 32' in the object space, which are located at different distances from the distal optical assembly 42. The change in the focal length causes a displacement of the axis intersection point 24 in the object space 26 in a direction along an optical axis 60 of the distal optical assembly 42 (see FIG. 4b). Through the displacement or respectively updating of the axis intersection point 24 with respect to an object plane 56, 58, in which objects are sharply imaged, a 3D representation is provided, the zero level of which always lies close to a screen surface or respectively a zero level of the playback device.

Deviating from this updating, it is also possible to freely set the axis intersection point 26 for the targeted displacement of the 3D zero level. The user is put in the position to be able to adjust the 3D representation so that the most comfortable and non-tiring work is possible.

While there has been shown and described what is considered to be preferred embodiments, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

REFERENCE LIST

2 Stereo video endoscope
4 Handle
6 Endoscope shaft
8 Distal tip
10 Entrance window
12 Distal section
14 Rotary wheel
18a Left lens system channel
18b Right lens system channel
20a Left viewing axis
20b Right viewing axis
22a Left optical axis
22b Right optical axis
24 Axis intersection point
26 Object space
28a Left optical system
28b Right optical system
30a Left image sensor
30b Right image sensor
32, 32' Object
34a Left displaceable lens group
34b Right displaceable lens group
40 Optical system
42 Distal optical assembly
44 Proximal optical assembly
46 Entrance lens
48 Deflection prism
50 Exit lens
52 Best operating point in the near range
53 Near range
54 Best operating point in the far range
55 Far range
56 Near object plane
58 Far object plane
60 Optical axis of the distal optical assembly
d1, d2 Object distance value

What is claimed is:

1. An optical system for a stereo video endoscope, the optical system comprising:
a distal optical assembly and a proximal optical assembly, the proximal optical assembly comprising a left lens system channel with a left optical axis and a right lens system channel with a right optical axis, the left and the right lens system channels being similarly configured and the left and the right optical axis being aligned parallel to each other, and the distal optical assembly being configured to couple light incident from an object space into the left lens system channel and into the right lens system channel of the proximal optical assembly, the distal optical assembly defining an axis intersection point in the object space, in which a left viewing axis of the left lens system channel and a right viewing axis of the right lens system channel intersect,
wherein the distal optical assembly having an adjustable focal length, wherein a change in a focal length of the distal optical assembly causes a displacement of the axis intersection point in the object space in a direction along an optical axis of the distal optical assembly;
the distal optical assembly comprises a zoom drive and the optical system further comprises a controller coupled with the zoom drive, wherein the controller is configured to control the zoom drive such that the axis intersection point is set alternatively to a best operating point in a near range or to a best operating point in a far range, wherein the best operating point in the near range and the best operating point in the far range lies in the object space and the best operating point in the far range is further removed from the distal optical assembly than the best operating point in the near range; and
the left lens system channel comprises at least one displaceable left optical element and the right lens system channel comprises at least one displaceable right optical element, wherein by displacing the left optical element, the sharpness of an image of an object located in the object space in the left lens system channel can be changed and by displacing the right optical element the sharpness of an image of the object located in the object space in the right lens system channel can be changed, and wherein the controller is configured to determine a left or a right object distance value and to control the zoom drive such that the axis intersection point is changed as a function of a left or a right object distance value.

2. The optical system according to claim 1, wherein the distal optical assembly comprises at least one displaceable optical element, wherein the displacement of the displaceable optical element causes the change in the focal length of the distal optical assembly.

3. An optical system according to claim 2, wherein the distal optical assembly, in a light incidence direction, comprises in succession, an entrance, a deflection prism and an exit lens, wherein the exit lens is the displaceable optical element.

4. A stereo video endoscope comprising the optical system according to claim 1.

5. A method for operating an optical system for a stereo video endoscope, the optical system comprising a distal optical assembly and a proximal optical assembly, the proximal optical assembly comprising a left lens system channel with a left optical axis and a right lens system channel with a right optical axis, the left and the right lens system channels being similarly configured and the left and the right optical axis being aligned parallel to each other, the distal optical assembly coupling light incident from an object space into the left lens system channel and into the right lens system channel of the proximal optical assembly, the distal optical assembly defining an axis intersection point in the object space, in which a left viewing axis of the left lens system channel and a right viewing axis of the right lens system channel intersect, wherein, for the imaging of objects in the object space, which are located at different distances from the distal optical assembly, changing a focal length of the distal optical assembly, wherein the change in the focal length of the distal optical assembly causes a displacement of the distal axis intersection point in the object space in a direction along an optical axis of the distal optical assembly;

wherein the distal optical assembly comprises a zoom drive, wherein with the zoom drive the axis intersection point is set alternatively to a best operating point in the near range or to a best operating point in the far range, and wherein the best operating point in a near range and the best operating point in a far range lie in the object space and the best operating point in a far range is further distanced from the distal optical assembly than the best operating point in the near range; and the left lens system channel comprises at least one displaceable left optical element and the right lens system channel comprises at least one displaceable right optical element, wherein by displacing the left optical element the sharpness of an image of an object located in an object space in the left lens system channel is changed and by displacing the right optical element the sharpness of an image of the object located in the object space in the right lens system channel is changed, and wherein a left or a right object distance value is determined and the zoom drive is controlled such that the axis intersection point changes as a function of the left or right object distance value.

6. The method according to claim 5, wherein at least one optical element of the distal optical assembly is displaced in order to change the focal length of the distal optical assembly.

* * * * *